(12) United States Patent
Cordi et al.

(10) Patent No.: US 6,486,143 B2
(45) Date of Patent: Nov. 26, 2002

(54) 6-AMINO- OR 6-HYDRAZINO-SULPHONYL-3-QUINOLYNYL-PHOSPHONIC ACID COMPOUNDS

(75) Inventors: Alex Cordi, Suresnes; Patrice Desos, Courbevoie; Pierre Lestage, La Celle Saint Cloud, all of (FR)

(73) Assignee: Les Laboratoires Servier, Neuilly-sur-Seine (FR)

( * ) Notice: Subject to any disclaimer, the term of this patent is extended or adjusted under 35 U.S.C. 154(b) by 0 days.

(21) Appl. No.: 09/784,632

(22) Filed: Feb. 15, 2001

(65) Prior Publication Data

US 2001/0031746 A1 Oct. 18, 2001

(30) Foreign Application Priority Data

Feb. 18, 2000 (FR) .............................. 00 02012

(51) Int. Cl.[7] ........................ A61K 31/675; A61K 31/47; C07F 9/38; C07D 215/36; A61P 25/00

(52) U.S. Cl. ........................ 514/82; 514/312; 514/313; 546/21; 546/154; 546/157; 546/172

(58) Field of Search .......................... 546/21, 157, 172; 514/82, 312, 313

(56) References Cited

U.S. PATENT DOCUMENTS 5,536,709 A  *  7/1996  Cordi .......................... 514/82
5,646,132 A  *  7/1997  Cordi .......................... 514/82

* cited by examiner

*Primary Examiner*—Evelyn Mei Huang

(57) ABSTRACT

The invention relates to a compound of formula (I):

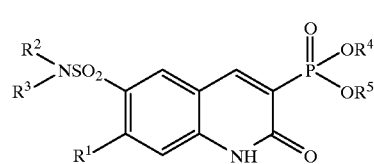

wherein:
$R^1$ represents halogen or a group $CF_3$,
$R^2$ represents hydrogen or alkyl or cycloalkyl,
$R^3$ is as defined in the description,
$R^4$ and $R^5$ represent hydrogen or alkyl, cycloalkyl, aryl or arylalkyl a group

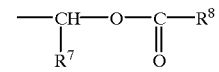

Medicaments.

16 Claims, No Drawings

6-AMINO- OR 6-HYDRAZINO-SULPHONYL-3-QUINOLYNYL-PHOSPHONIC ACID COMPOUNDS

FIELD OF THE INVENTION

The present invention relates to new 6-amino- or 6-hydrazino-sulphonyl-3-quinolylphosphonic acid compounds and to compositions containing them.

DESCRIPTION OF THE PRIOR ART AND BACKGROUND OF THE INVENTION

The prior art describes compounds that are capable of countering the excitatory and toxic effects of the excitatory amino acids (EAA) by blocking the initial activation of the AMPA (α-amino-3-hydroxy-5-methyl-4-isoxazolepropionic acid)/kainate receptor (EP 0 640 612). Their usefulness is accordingly recognised for inhibiting pathological phenomena, especially neurotoxic phenomena associated with hyperactivation of the neurotransmission paths to the excitatory amino acids. Those compounds pose serious problems of nephrotoxicity, however, as has also been shown to be the case for other non-NMDA (N-methyl-D-aspartate) antagonists of reference, such as, for example, 6-nitro-7-sulphamoyl-benzo[f]quinoxaline-2,3-dione (NBQX) (*Journal of Cerebral Blood Flow and Metabolism*, 1994, 14, 251–261).

The Applicant has discovered new compounds that have more powerful non-NMDA antagonist properties than do the compounds of the prior art, with greatly reduced associated nephrotoxicity. Those compounds are therefore new and are potential powerful therapeutic agents for the acute, and also chronic, treatment of neurological and psychological disorders involving those amino acids, for example degenerative disorders such as cerebrovascular accident, cerebral or spinal traumatism, epilepsy, chronic neurodegenerative diseases such as Alzheimer's disease, schizophrenia, lateral amyotrophic sclerosis or Huntington's chorea.

DETAILED DESCRIPTION OF THE INVENTION

More especially, the present invention relates to compounds of formula (I):

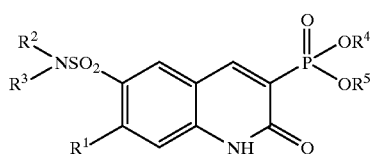

wherein:
$R^1$ represents a halogen atom or a trifluoromethyl group,
$R^2$ represents a hydrogen atom or an alkyl or cycloalkyl group,
$R^3$ represents an alkyl, cycloalkyl, aryl, arylalkyl, alkoxy, aryloxy, arylalkoxy, hydroxy, aminoalkyl, alkylaminoalkyl, dialkylaminoalkyl, alkylcarbonyl, arylcarbonyl or arylalkylcarbonyl group or an $NHR^6$ group (wherein $R^6$ represents a hydrogen atom or an alkyl, cycloalkyl, aryl, alkylcarbonyl, arylcarbonyl, arylalkyl or arylalkylcarbonyl group),
or $R^2$ and $R^3$ together form with the nitrogen atom carrying them a ring having 5 or 6 carbon atoms, in which one of the carbon atoms can be replaced by an oxygen, nitrogen or sulphur atom or by an SO or $SO_2$ group or by an $NR_a$ group (wherein $R_a$ represents a hydrogen atom or an alkyl, cycloalkyl, aryl or arylalkyl group),
$R^4$ and $R^5$, which may be identical or different, represent a hydrogen atom or an alkyl, cycloalkyl, aryl or arylalkyl group or a group

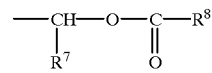

(wherein $R^7$ and $R^8$, which may be identical or different, represent a hydrogen atom or an alkyl, cycloalkyl or aryl group),
it being understood that:
"alkyl" is understood to mean a linear or branched alkyl group containing from 1 to 6 carbon atoms,
"alkoxy" is understood to mean a linear or branched alkoxy group containing from 1 to 6 carbon atoms,
"cycloalkyl" is understood to mean a cyclic alkyl group containing from 3 to 8 carbon atoms,
"aryl" is understood to mean the groups phenyl or naphthyl, it being possible for those groups to be unsubstituted or substituted by from 1 to 3 groups selected from alkyl, cycloalkyl, hydroxy, alkoxy, amino, alkylamino, dialkylamino, cyano, nitro, polyhaloalkyl, $SO_2NR^9R^{10}$ (wherein $R^9$ and $R^{10}$, which may be identical or different, represent a hydrogen atom or an alkyl, cycloalkyl or aryl group) and halogen atoms,
their enantiomers and diastereoisomers and addition salts thereof with a pharmaceutically acceptable acid or base.

Among the pharmaceutically acceptable acids there may be mentioned by way of non&-limiting example hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid, oxalic acid, etc.

Among the pharmaceutically acceptable bases there may be mentioned by way of non-limiting example sodium hydroxide, potassium hydroxide, triethylamine, tert-butylamine, etc.

The preferred compounds of the invention are compounds of formula (I) wherein $R^1$ represents a chlorine atom.

The preferred groups $R^3$ are the alkyl group (such as, for example, methyl or propyl), the dialkylaminoalkyl group (such as, for example, dimethylaminoethyl), the aryl group (such as, for example, phenyl), the arylcarbonyl group (such as, for example, benzoyl) or the group NHCOR wherein R represents an alkyl or aryl group.

An advantageous aspect of the invention relates to compounds of formula (I) wherein $R^2$ is a hydrogen atom, or an alkyl group.

When $R^2$ is a hydrogen atom, $R^3$ advantageously represents the groups cycloalkyl, aryl, arylalkyl, alkoxy, aryloxy, arylalkoxy, hydroxy, aminoalkyl, alkylaminoalkyl, dialkylaminoalkyl, alkylcarbonyl, arylcarbonyl, arylalkylcarbonyl or $NHR^6$.

When $R^2$ is an alkyl group, $R^3$ advantageously represents the group alkyl.

The hydrogen atom is the preferred meaning for the substituents $R^4$ and $R^5$.

More especially still, the invention relates to compounds of formula (I) which are:
7-chloro-2-oxo-6-[(n-propylamino)sulphonyl]-1,2-dihydro-3-quinolylphosphonic acid, 7-chloro-6-[(methylamino)sulphonyl]-2-oxo-1,2-dihydro-3-quinolylphosphonic acid, 6-(anilinosulphonyl)-7-chloro-2-oxo-1,2-dihydro-3-quinolylphosphonic acid, 6-[(2-benzoylhydrazino)sulphonyl]-7-chloro-2-oxo-1,2-dihydro-3-quinolylphosphonic acid, 7-chloro-6-[(2-{4-[(di-n-propylamino)sulphonyl]benzoyl}hydrazino)sulphonyl]-2-oxo-1,2-dihydro-3-quinolylphosphonic acid, and 7-chloro-6-({[2-(dimethylamino)ethyl]amino}sulphonyl)-2-oxo-1,2-dihydro-3-quinolylphosphonic acid hydrobromide.

The enantiomers, diastereoisomers and pharmaceutically acceptable addition salts with an acid or a base of the preferred compounds of the invention form an integral part of the invention.

The invention relates also to a process for the preparation of compounds of formula (I), characterised in that there is used as starting material a compound of formula (II):

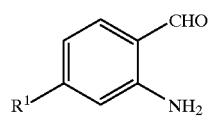

(II)

wherein $R^1$ is as defined for formula (I), which is condensed, in the presence of a base, such as, for example, pyridine, with a compound of formula (III):

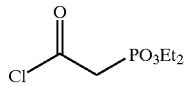

(III)

to yield a compound of formula (IV):

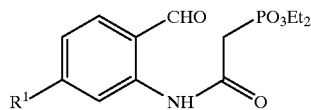

(IV)

wherein $R^1$ is as defined hereinbefore, which is cyclised in the presence of a catalytic amount of piperidine to obtain a compound of formula (V):

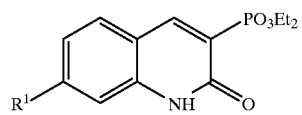

(V)

wherein $R^1$ is as defined hereinbefore, which is subjected to a mixture of nitric acid and sulphuric acid to yield a compound of formula (VI):

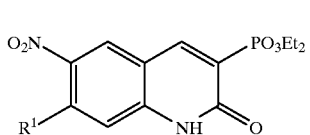

(VI)

wherein $R^1$ is as defined hereinbefore, which is reduced using palladium-on-carbon in the presence of hydrogen or iron in a dilute alcoholic medium to yield a compound of formula (VII):

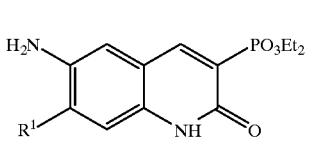

(VII)

wherein $R^1$ is as defined hereinbefore, which is subjected, after conversion to the corresponding diazonium salt, to the action of sulphur dioxide in the presence of $CuCl_2$ to yield a compound of formula (VIII):

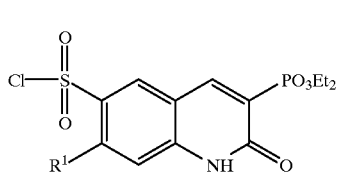

(VIII)

wherein $R^1$ is as defined hereinbefore, which is condensed with a compound of formula $HNR^2R^3$ wherein $R^2$ and $R^3$ are as defined for formula (I) to yield a compound of formula (I/a), a particular case of the compounds of formula (I):

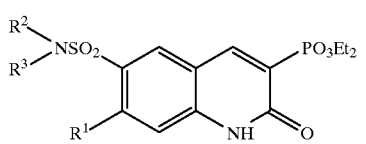

(I/a)

wherein $R^1$, $R^2$ and $R^3$ are as defined hereinbefore, which is partially or totally deprotected in the presence of, for example, trimethylsilane bromide to yield a compound of formula (I/b), a particular case of the compounds of formula (I):

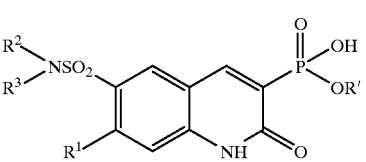

(I/b)

wherein $R^1$, $R^2$ and $R^3$ are as defined hereinbefore and $R^1$ represents a hydrogen atom or an ethyl group, which may be condensed with a compound of formula (IX):

wherein R" represents an alkyl, aryl or arylalkyl group or a group

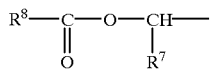

(wherein $R^7$ and $R^8$ are as defined for formula (I)), to obtain a compound of formula (I/c), a particular case of the compounds of formula (I):

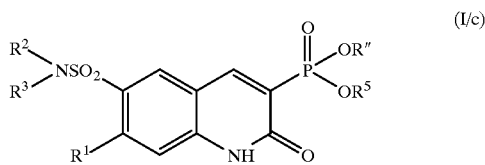

wherein $R^1$, $R^2$, $R^3$, $R^5$ and R" are as defined hereinbefore,
which compounds of formulae (I/a) to (I/c) constitute the totality of the compounds of formula (I), and can be purified according to a conventional separation technique, are converted, if desired, into their addition salts with a pharmaceutically acceptable acid or base, and separated, where appropriate, into their isomers according to a conventional separation technique.

The compounds of the invention have very valuable pharmacological properties since they are powerful inhibitors of the AMPA receptor, and they are moreover selective since they do not affect the NMDA receptor and therefore do not have any of the side-effects described for NMDA antagonists, and especially do not have the nephrotoxicity associated with a number of AMPA/non-NMDA antagonists. The use of those compounds as inhibitors of pathological phenomena associated with hyperactivation of the neurotransmission paths to the excitatory amino acids will therefore be particularly appreciated in the acute, and especially chronic, treatment of neurological and psychological disorders involving those amino acids, for example degenerative disorders such as cerebrovascular accident, cerebral or spinal traumatism, epilepsy, chronic neurodegenerative diseases such as Alzheimer's disease, schizophrenia, lateral amyotrophic sclerosis or Huntington's chorea.

The present invention relates also to pharmaceutical compositions comprising as active ingredient at least one compound of formula (I) alone or in combination with one or more pharmaceutically acceptable excipients.

Among the pharmaceutical compositions according to the invention, there may be mentioned more especially those that are suitable for oral, parenteral, nasal, per- or transcutaneous, rectal, perlingual, ocular or respiratory administration, especially tablets or dragées, sublingual tablets, sachets, paquets, gelatin capsules, glossettes, lozenges, suppositories, creams, ointments, dermal gels and drinkable or injectable ampoules.

The dosage varies according to the sex, age and weight of the patient, the route of administration, the nature of the therapeutic indication, or any associated treatments and ranges from 50 mg to 1 g per 24 hours in 1 or more administrations.

The following Examples illustrate the invention and do not limit it in any way.

EXAMPLE 1

7-Chloro-2-oxo-6-[(n-propylamino)sulphonyl]-1,2-dihydro-3-quinolylphosphonic Acid Diethyl Ester Step A: [(5-Chloro-2-formyl-phenylcarbamoyl)methyl] phosphonic Acid Diethyl Ester Pyridine (3.7 ml, 45.7 mmol) is added to a solution of 2-amino-4-chlorobenzaldehyde (6.18 g, 39.7 mmol) in 170 ml of anhydrous toluene, followed dropwise by a solution of chlorocarbonylmethylphosphonic acid diethyl ester (9.8 g, 45.7 mmol) in 15 ml of anhydrous toluene whilst maintaining the reaction mixture at a temperature of less than 30° C. When the addition is complete, the mixture is stirred for 1 hour at room temperature. The reaction mixture is washed several times with water and then with a 1N HCl solution, and then again with water. Finally the mixture is washed with an aqueous saturated NaCl solution. The organic phase is dried over $MgSO_4$, and filtration is carried out, followed by evaporation to obtain the expected crude product in the form of an orange oil. The crude product is used in the following step.

Step B: (7-Chloro-2-oxo-1,2-dihydro-3-quinolyl) phosphonic Acid Diethyl Ester

In a round-bottomed flask on which there is mounted a Dean-Stark apparatus there is refluxed for 4 hours, with vigorous stirring, all of the compound obtained in Step A dissolved in 300 ml of toluene and 0.3 ml of piperidine. The batch is left to crystallise at room temperature and the resulting pale yellow solid is filtered off.

Melting point: 210–213° C.

| | Elemental microanalysis: | | | |
|---|---|---|---|---|
| | C % | H % | N % | Cl % |
| calculated | 49.46 | 4.79 | 4.44 | 11.23 |
| found | 49.77 | 4.78 | 4.46 | 11.63 |

Step C: (7-Chloro-6-nitro-2-oxo-1,2-dihydro-3-quinolyl) phosphonic Acid Diethyl Ester 55 ml of nitric acid are added dropwise to a solution of 55 ml of 96% sulphuric acid cooled in an ice bath, and then (7-chloro-2-oxo-1,2-dihydro-3-quinolyl)-phosphonic acid diethyl ester (14.7 g, 46.6 mmol) is added in portions whilst maintaining the temperature at less than or equal to 5° C. When the addition is complete, stirring is continued for 15 minutes and then the ice bath is withdrawn and the reaction mixture is brought to room temperature over a period of about 1 hour 30 minutes. The solution is poured into ice and the precipitate is stirred to obtain a filterable solid. Filtration is carried out, followed by washing with water to neutrality and drying in vacuo. The solid is suspended in 210 ml of ethanol at reflux; the batch is left to cool and filtered to obtain the title product after drying.

Melting point: 258–262° C.

| | Elemental microanalysis: | | | |
|---|---|---|---|---|
| | C % | H % | N % | Cl % |
| calculated | 43.29 | 3.91 | 7.77 | 9.83 |
| found | 43.33 | 4.06 | 7.60 | 9.70 |

Step D: (6-Amino-7-chloro-2-oxo-1,2-dihydro-3-quinolyl)phosphonic Acid Diethyl Ester A suspension of the compound obtained in Step C (7.0 g, 19.4 mmol), powdered iron (10.8 g, 194 mmol) and ammonium chloride (10.4 g, 194 mmol) is stirred at reflux for 1 hour in a mixture of 270 ml of methanol and 90 ml of water. The suspension is filtered hot over Celite and the solid is rinsed several times with methanol. The filtrate is evaporated to dryness and the residue is suspended in water. The solid is filtered off, rinsed with water and dried to obtain the title product in the form of orange crystals.

Melting point: 255–260° C.

| | Elemental microanalysis: | | |
|---|---|---|---|
| | C % | H % | N % |
| calculated | 47.22 | 4.88 | 8.47 |
| found | 47.06 | 4.99 | 8.08 |

Step E: (7-Chloro-6-chlorosulphonyl-2-oxo-1,2-dihydro-3-quinolyl)phosphonic Acid Diethyl Ester A solution of 13.4 ml of acetic acid and 2.25 ml of water is saturated with $SO_2$ by bubbling $SO_2$ gas through for 15 minutes. In parallel, at 5° C. there is prepared a solution of the compound obtained in Step D (3.34 g, 10.1 mmol) in a mixture of 10 ml of glacial acetic acid and 17 ml of concentrated HCl. To that solution there is added dropwise a solution of sodium nitrite (767 mg, 11.11 mmol) previously dissolved in 5 ml of water, and the reaction mixture is stirred for 30 minutes at 5° C. $CuCl_2.2H_2O$ (689 mg, 4.04 mmol) is added to the solution saturated with $SO_2$, and the resulting suspension is cooled to 5° C. The diazonium chloride solution prepared above is added dropwise to that solution. The mixture is stirred for 1 hour at 5° C., and then for 3 hours, allowing it to return to room temperature. The reaction mixture is poured into ice and the precipitate is filtered off and rinsed with water. Drying yields the title product in the form of a pale yellow powder.

Melting point: 190–200° C.

| | Elemental microanalysis: | | | | |
|---|---|---|---|---|---|
| | C % | H % | N % | S % | Cl % |
| calculated | 37.70 | 3.41 | 3.38 | 7.74 | 17.12 |
| found | 38.04 | 3.47 | 3.40 | 7.74 | 17.16 |

Step F: 7-Chloro-2-oxo-6-[(n-propylamino)sulphonyl]-1,2-dihydro-3-quinolylphosphonic Acid Diethyl Ester A suspension of the compound obtained in Step E (1.26 g, 3.0 mmol) with n-propylamine (9.0 mmol) in 30 ml of acetonitrile is stirred for 3 hours. Evaporation to dryness is carried out, the residue is then taken up in 1N HCl and extraction is carried out with ethyl acetate. Drying over $MgSO_4$ and evaporation of the organic phase yield a residue which is taken up in ether and filtered to yield the title product.

Melting point: >300° C.

| | Elemental microanalysis: | | | |
|---|---|---|---|---|
| | C % | H % | N % | S % |
| calculated | 43.99 | 5.08 | 6.41 | 7.34 |
| found | 43.99 | 5.08 | 6.24 | 7.07 |

EXAMPLE 2

7-Chloro-2-oxo-6-[(n-propylamino)sulphonyl]-1,2-dihydro-3-quinolylphosphonic Acid 25.3 mmol of bromotrimethylsilane are added to a suspension of the compound obtained in Example 1 (2.53 mmol) in 30 ml of anhydrous acetonitrile. Stirring is carried out at reflux for 1 hour, followed by evaporation to dryness. The residue is dried in vacuo and taken up in methanol. The suspension is stirred for 30 minutes and becomes increasingly thick. The precipitate is filtered off and rinsed with a small amount of methanol to obtain the title product.

Melting point: >300° C.

| | Elemental microanalysis: | | | | |
|---|---|---|---|---|---|
| | C % | H % | N % | S % | Cl % |
| calculated | 37.86 | 3.71 | 7.36 | 8.42 | 9.31 |
| found | 37.60 | 3.83 | 7.07 | 7.78 | 10.06 |

The following Examples are obtained according to procedures similar to those of Examples 1 and 2 starting from the appropriate substrates.

EXAMPLE 3

7-Chloro-6-[(di-n-propylamino)sulphonyl]-2-oxo-1,2-dihydro-3-quinolylphosphonic Acid Diethyl Ester The procedure is as for Example 1, replacing n-propylamine by dipropylamine in Step F.

Melting point: 172–175° C.

EXAMPLE 4

7-Chloro-6-[(di-n-propylamino)sulphonyl]-2-oxo-1,2-dihydro-3-quinolylphosphonic Acid The procedure is as for Example 2 starting from the compound obtained in Example 3.

Melting point: >300° C.

| | Elemental microanalysis: | | | | |
|---|---|---|---|---|---|
| | C % | H % | N % | S % | Cl % |
| calculated | 42.61 | 4.77 | 6.63 | 7.58 | 8.38 |
| found | 42.40 | 4.78 | 6.48 | 7.35 | 8.95 |

EXAMPLE 5

7-Chloro-6-[(methylamino)sulphonyl]-2-oxo-1,2-dihydro-3-quinolylphosphonic Acid Diethyl Ester The procedure is as for Example 1, replacing n-propylamine by methylamine in Step F. The reaction is carried out in water. After the batch has been rendered acidic with 3N HCl, a precipitate is obtained, which is filtered off and which corresponds to the title product.

Melting point: 261–265° C.

| Elemental microanalysis: | | | | |
|---|---|---|---|---|
| | C % | H % | N % | S % |
| calculated | 41.13 | 4.44 | 6.85 | 7.84 |
| found | 41.05 | 4.39 | 6.83 | 7.86 |

EXAMPLE 6
7-Chloro-6-[(methylamino)sulphonyl]-2-oxo-1,2-dihydro-3-quinolylphosphonic Acid The procedure is as for Example 2 starting from the compound obtained in Example 5.

Melting point: >300° C.

| Elemental microanalysis: | | | | | |
|---|---|---|---|---|---|
| | C % | H % | N % | S % | Cl % |
| calculated | 34.06 | 2.86 | 7.94 | 9.09 | 10.05 |
| found | 34.20 | 3.01 | 7.75 | 8.98 | 10.18 |

EXAMPLE 7
7-Chloro-6-[(dimethylamino)sulphonyl]-2-oxo-1,2-dihydro-3-quinolylphosphonic Acid Diethyl Ester The procedure is as for Example 5, replacing n-propylamine by dimethylamine in Step F.

Melting point: 237–240° C.

| Elemental microanalysis: | | | | | |
|---|---|---|---|---|---|
| | C % | H % | N % | S % | Cl % |
| calculated | 42.61 | 4.77 | 6.63 | 7.58 | 8.38 |
| found | 42.41 | 4.71 | 6.46 | 7.31 | 8.12 |

EXAMPLE 8
7-Chloro-6-[(dimethylamino)sulphonyl]-2-oxo-1,2-dihydro-3-quinolylphosphonic Acid The procedure is as for Example 2 starting from the compound obtained in Example 7.

Melting point. 256–259° C.

| Elemental microanalysis: | | | | | |
|---|---|---|---|---|---|
| | C % | H % | N % | S % | Cl % |
| calculated | 34.06 | 2.86 | 7.94 | 9.09 | 10.05 |
| found | 34.20 | 3.01 | 7.75 | 8.98 | 10.18 |

EXAMPLE 9
7-Chloro-6-(4-morpholinylsulphonyl)-2-oxo-1,2-dihydro-3-quinolylphosphonic Acid Diethyl Ester The procedure is as for Example 1, replacing n-propylamine by morpholine in Step F.

EXAMPLE 10
7-Chloro-6-(4-morpholinylsulphonyl)-2-oxo-1,2-dihydro-3-quinolylphosphonic Acid The procedure is as for Example 2 starting from the compound obtained in Example 9.

Melting point: >260° C.

| Elemental microanalysis: | | | | | |
|---|---|---|---|---|---|
| | C % | H % | N % | S % | Cl % |
| calculated | 38.20 | 3.45 | 6.85 | 7.84 | 8.67 |
| found | 37.90 | 3.64 | 6.55 | 7.59 | 8.70 |

EXAMPLE 11
7-Chloro-6-({[2-(dimethylamino)ethyl]amino}sulphonyl)-2-oxo-1,2-dihydro-3-quinolylphosphonic Acid Diethyl Ester Hydrobromide The procedure is as for Example 1, replacing n-propylamine by dimethylaminoethylamine in Step F. The reaction is carried out in dichloromethane and, after washing with water, purification is carried out over a silica column (eluant: dichloromethane/methanol: 9/1) to yield the title product.

Melting point: 166–171° C.

| Elemental microanalysis: | | | | |
|---|---|---|---|---|
| | C % | H % | N % | S % |
| calculated | 43.83 | 5.41 | 9.02 | 6.88 |
| found | 43.50 | 5.48 | 8.70 | 7.05 |

EXAMPLE 12
7-Chloro-6-({[2-(dimethylamino)ethyl]amino}sulphonyl)-2-oxo-1,2-dihydro-3-quinolylphosphonic Acid Hydrobromide The procedure is as for Example 2 starting from the compound obtained in Example 11.

Melting point: 216–220° C.

| Elemental microanalysis: | | | | | |
|---|---|---|---|---|---|
| | C % | H % | N % | S % | Br % |
| calculated | 31.82 | 3.70 | 8.56 | 6.53 | 16.28 |
| found | 32.15 | 3.98 | 8.37 | 6.07 | 15.89 |

EXAMPLE 13
6-(Anilinosulphonyl)-7-chloro-2-oxo-1,2-dihydro-3-quinolylphosphonic Acid Diethyl Ester The procedure is as for Example 1, replacing n-propylamine by aniline in Step F.

Melting point: 139–141° C.

| Elemental microanalysis: | | | | |
|---|---|---|---|---|
| | C % | H % | N % | S % |
| calculated | 48.47 | 4.28 | 5.95 | 6.81 |
| found | 48.60 | 4.30 | 5.91 | 6.90 |

EXAMPLE 14
6-(Anilinosulphonyl)-7-chloro-2-oxo-1,2-dihydro-3-quinolylphosphonic Acid The procedure is as for Example 2 starting from the compound obtained in Example 13.

Melting point: 249–253° C.

| Elemental microanalysis: | | | | | |
|---|---|---|---|---|---|
| | C % | H % | N % | S % | Cl % |
| calculated | 43.44 | 2.92 | 6.75 | 7.73 | 8.55 |
| found | 43.53 | 2.87 | 6.64 | 7.82 | 9.06 |

EXAMPLE 15
6-[(2-Benzoylhydrazino)sulphonyl]-7-chloro-2-oxo-1,2-dihydro-3-quinolylphosphonic Acid Diethyl Ester The procedure is as for Example 1, replacing n-propylamine by benzoylhydrazine in Step F. The reaction is carried out in dichloromethane. The title product precipitates from the reaction mixture and is separated off by filtration.

Melting point: 202–204° C.

| Elemental microanalysis: | | | | | |
|---|---|---|---|---|---|
| | C % | H % | N % | S % | Cl % |
| calculated | 46.75 | 4.12 | 8.18 | 6.24 | 6.90 |
| found | 46.66 | 4.06 | 8.01 | 6.18 | 7.41 |

EXAMPLE 16
6-[(2-Benzoylhydrazino)sulphonyl]-7-chloro-2-oxo-1,2-dihydro-3-quinolylphosphonic Acid The procedure is as for Example 2 starting from the compound obtained in Example 15.

Melting point: 242–244° C.

| Elemental microanalysis: | | | | | |
|---|---|---|---|---|---|
| | C % | H % | N % | S % | Cl % |
| calculated | 41.98 | 2.86 | 9.18 | 7.00 | 7.74 |
| found | 42.12 | 2.80 | 8.95 | 7.05 | 7.92 |

EXAMPLE 17
6-[(2-Acetylhydrazino)-sulphonyl]-7-chloro-2-oxo-1,2-dihydro-3-quinolylphosphonic Acid Diethyl Ester The procedure is as for Example 15, replacing benzoylhydrazine by acetylhydrazine in Step F.

Melting point: 125–160° C.

EXAMPLE 18
6-[(2-Acetylhydrazino)-sulphonyl]-7-chloro-2-oxo-1,2-dihydro-3-quinolylphosphonic Acid The procedure is as for Example 2 starting from the compound obtained in Example 17.

Melting point: >300° C.

| Elemental microanalysis: | | | | | |
|---|---|---|---|---|---|
| | C % | H % | N % | S % | Cl % |
| calculated | 33.39 | 2.80 | 10.62 | 8.10 | 8.96 |
| found | 33.61 | 3.09 | 10.18 | 7.70 | 8.23 |

EXAMPLE 19

7-Chloro-6-[(2-{4-[(di-n-propylamino)sulphonyl]benzoyl}-hydrazino)sulphonyl]-2-oxo-1,2-dihydro-3-quinolylphosphonic Acid Diethyl Ester The procedure is as for Example 1, replacing n-propylamine by p-(dipropylaminosulphonyl) benzoylhydrazine in Step F.

Melting point: 288–290° C.

| Elemental microanalysis: | | | | | |
|---|---|---|---|---|---|
| | C % | H % | N % | S % | Cl % |
| calculated | 46.12 | 5.06 | 8.27 | 9.47 | 5.24 |
| found | 45.74 | 5.09 | 8.46 | 9.77 | 5.83 |

EXAMPLE 20
7-Chloro-6-[(2-{4-[(di-n-propylamino)sulphonyl]benzoyl}-hydrazino)sulphonyl]-2-oxo-1,2-dihydro-3-quinolylphosphonic Acid The procedure is as for Example 2 starting from the compound obtained in Example 19.

Melting point: 210–214° C.

| Elemental microanalysis: | | | | | |
|---|---|---|---|---|---|
| | C % | H % | N % | S % | Cl % |
| calculated | 42.55 | 4.22 | 9.02 | 10.33 | 5.71 |
| found | 42.35 | 4.45 | 8.69 | 10.52 | 6.21 |

EXAMPLE 21
7-Chloro-2-oxo-6-({2-[4-[(trifluoromethyl)benzoyl]hydrazino}-sulphonyl)-1,2-dihydro-3-quinolylphosphonic Acid Diethyl Ester The procedure is as for Example 15, replacing benzoylhydrazine by p-(trifluoromethyl)benzoylhydrazine in Step F.

Melting point: 281–282° C.

| Elemental microanalysis: | | | | |
|---|---|---|---|---|
| | C % | H % | N % | S % |
| calculated | 43.35 | 3.46 | 7.22 | 5.51 |
| found | 43.73 | 3.55 | 7.24 | 5.43 |

EXAMPLE 22
7-Chloro-2-oxo-6-({2-[4-[(trifluoromethyl)benzoyl]-hydrazino}sulphonyl)-1,2-dihydro-3-quinolylphosphonic Acid The procedure is as for Example 2 starting from the compound obtained in Example 21.

Melting point: 278–282° C.

| Elemental microanalysis: | | | | |
|---|---|---|---|---|
| | C % | H % | N % | S % |
| calculated | 38.83 | 2.30 | 7.99 | 6.10 |
| found | 38.80 | 2.26 | 7.78 | 6.01 |

EXAMPLE 23

6-[(Benzoylamino)sulphonyl]-7-chloro-2-oxo-1,2-dihydro-3-quinolylphosphonic Acid Diethyl Ester The procedure is as for Example 1, replacing n-propylamine by benzoylamine in Step F.

Melting point: >300° C.

The compound of Example 23 can also be obtained in the following manner:

Step A: 6-(Aminosulphonyl)-7-chloro-2-oxo-1,2-dihydro-3-quinolylphosphonic Acid Diethyl Ester A suspension of the compound obtained in Step E of Example 1 (1.26 g, 3.0 mmol) in 18 ml of 28% ammonium hydroxide solution is stirred. After a few minutes the batch is observed to pass into solution. Stirring is maintained for 30 minutes and the reaction mixture is rendered acidic with 4N HCl. A few ml of ethyl acetate are added with stirring and precipitation occurs. The precipitate is filtered off and dried in vacuo to yield the title product in the form of a cream-coloured powder.

Melting point. 288–290° C.

Step B: 6-[(Benzoylamino)sulphonyl]-7-chloro-2-oxo-1,2-dihydro-3-quinolylphosphonic Acid Diethyl Ester A solution of benzoic acid (111 mg, 0.912 mmol) in 3 ml of anhydrous THF containing 173 mg (1.06 mmol) of carbonyldiimidazole is stirred for 45 minutes at reflux. In parallel, there is prepared a suspension of 300 mg (0.760 mmol) of the compound obtained in Step A in 3 ml of THF, to which there is added 0.125 ml (0.836 mmol) of DBU. Stirring is carried out for 15 minutes at room temperature, and then the benzoic acid solution prepared above is added thereto. The mixture is heated for 3 hours at 60° C. The reaction mixture is cooled in an ice bath and rendered acidic by the addition of 1N HCl. Extraction is carried out with ethyl acetate. The organic phases are combined and washed with a saturated NaCl solution and then dried over $MgSO_4$. After evaporation, the residue is chromatographed over a silica column whilst eluting with a gradient (95/5-90/10) of $CH_2Cl_2$/MeOH. The title product is obtained in the form of a white solid.

EXAMPLE 24

6-[(Benzoylamino)sulphonyl]-7-chloro-2-oxo-1,2-dihydro-3-quinolylphosphonic Acid The procedure is as for Example 2 starting from the compound obtained in Example 23.

Melting point: 236–241° C.

| Elemental microanalysis: | | | | | |
|---|---|---|---|---|---|
| | C % | Cl % | H % | N % | S% |
| calculated | 43.40 | 8.01 | 2.73 | 6.33 | 7.24 |
| found | 43.38 | 8.18 | 2.86 | 6.17 | 7.20 |

EXAMPLE 25

7-Chloro-6-[({4-[(dipropylamino)sulphonyl]benzoyl}amino)sulphonyl]-2-oxo-1,2-dihydro-3-quinolylphosphonic Acid Diethyl Ester The procedure is as for Example 23, replacing benzoic acid by 4-[(di-n-propylamino)sulphonyl]benzoic Acid.

Melting point. 197–200° C.

| Elemental microanalysis: | | | | |
|---|---|---|---|---|
| | C % | H % | N % | S% |
| calculated | 47.17 | 5.02 | 6.35 | 9.69 |
| found | 46.83 | 5.07 | 6.24 | 9.84 |

EXAMPLE 26

7-Chloro-6-[({4-[(dipropylamino)sulphonyl]benzoyl}amino)sulphonyl]-2-oxo-1,2-dihydro-3-quinolylphosphonic Acid The procedure is as for Example 2 starting from the compound obtained in Example 25.

Melting point: 202–206° C.

| Elemental microanalysis: | | | | | |
|---|---|---|---|---|---|
| | C % | H % | N % | S % | Cl% |
| calculated | 43.60 | 4.16 | 6.93 | 10.58 | 5.85 |
| found | 43.81 | 4.27 | 6.72 | 10.62 | 5.96 |

EXAMPLE 27

7-Chloro-6-[(methoxyamino)sulphonyl]-2-oxo-1,2-dihydro-3-quinolylphosphonic Acid Diethyl Ester The procedure is as for Example 1, replacing n-propylamine by methoxyamine hydrochloride in Step F and carrying out the reaction in an acetonitrile/water mixture.

Melting point: 176–180° C.

| Elemental microanalysis: | | | | | |
|---|---|---|---|---|---|
| | C % | H % | N % | S % | Cl% |
| calculated | 39.58 | 4.27 | 6.59 | 7.55 | 8.35 |
| found | 39.43 | 4.35 | 6.39 | 7.41 | 8.89 |

EXAMPLE 28

7-Chloro-6-[(methoxyamino)sulphonyl]-2-oxo-1,2-dihydro-3-quinolylphosphonic Acid The procedure is as for Example 2 starting from the compound obtained in Example 27.

Melting point: 259–260° C.

| Elemental microanalysis: | | | | |
|---|---|---|---|---|
| | C % | H % | N % | S% |
| calculated | 32.58 | 2.73 | 7.60 | 8.70 |
| found | 32.78 | 2.74 | 7.40 | 8.73 |

EXAMPLE 29

6-[(n-Dipropylamino)sulphonyl]-2-oxo-7-(trifluoromethyl)-1,2-dihydro-3-quinolylphosphonic Acid Diethyl Ester The protocols of Steps A–G of Example 29 are identical to those of Example 1, replacing 2-amino-4-chlorobenzaldehyde by 2-amino-4-trifluoromethylbenzaldehyde in Step A of Example 29, and carrying out the reduction step of Step D with the couple Pd—C/-ammonium formate instead of the couple Fe/$NH_4Cl$ in a dilute alcoholic medium.

Step A: [(5-Trifluoromethyl-2-formyl-phenylcarbamoyl)-methyl]-phosphonic Acid Diethyl Ester
Melting point: 62–64° C.

Elemental microanalysis:

|  | C % | H % | N% |
|---|---|---|---|
| calculated | 45.79 | 4.67 | 3.81 |
| found | 45.89 | 4.66 | 3.76 |

Step B: (7-Trifluoromethyl-2-oxo-1,2-dihydro-3-quinolyl)phosphonic Acid Diethyl Ester
Melting point: 151° C.

Elemental microanalysis:

|  | C % | H % | N% |
|---|---|---|---|
| calculated | 48.15 | 4.33 | 4.01 |
| found | 48.19 | 4.32 | 3.92 |

Step C: (7-Trifluoromethyl-6-nitro-2-oxo-1,2-dihydro-3-quinolyl)phosphonic Acid Diethyl Ester
Melting point: 209–215° C.

Elemental microanalysis:

|  | C % | H % | N% |
|---|---|---|---|
| calculated | 42.65 | 3.58 | 7.11 |
| found | 42.86 | 3.58 | 6.78 |

Step D: (6-Amino-7-trifluoromethyl-2-oxo-1,2-dihydro-3-quinolyl)phosphonic Acid Diethyl Ester A mixture of 490 mg (1.24 mmol) of the compound obtained in Step C, 650 mg (12.4 mmol) of ammonium formate and 120 mg of 10% Pd/C in 50 ml of ethanol is stirred at reflux for 1 hour. The catalyst is filtered off over a membrane, the filtrate is evaporated to dryness and the residue is taken up in water. The suspension is filtered, rinsed with water, suction-filtered and dried in vacuo to obtain the title product in the form of a yellow solid.
Melting point: 240–244° C.

Elemental microanalysis:

|  | C % | H % | N% |
|---|---|---|---|
| calculated | 46.16 | 4.43 | 7.69 |
| found | 46.26 | 4.37 | 7.62 |

Step E: (7-Trifluoromethyl-6-chlorosulphonyl-2-oxo-1,2-dihydro-3-quinolyl)phosphonic Acid Diethyl Ester
Melting point: 165–171° C.

Elemental microanalysis:

|  | C % | H % | N % | S % | Cl% |
|---|---|---|---|---|---|
| calculated | 34.56 | 3.15 | 3.13 | 7.16 | 7.92 |
| found | 37.54 | 3.20 | 3.18 | 7.05 | 7.97 |

Step F: 6-[(Di-n-propylamino)sulphonyl]-2-oxo-7-(trifluoromethyl)-1,2-dihydro-3-quinolylphosphonic Acid Diethyl Ester
The procedure is as for Step F of Example 1, replacing n-propylamine by dipropylamine.

EXAMPLE 30

6-[(Di-n-propylamino)sulphonyl]-2-oxo-7-(trifluoromethyl)-1,2-dihydro-3-quinolylphosphonic Acid
The procedure is as for Example 2 starting from the compound obtained in Example 29.
Melting point: >260° C.

Elemental microanalysis:

|  | C % | H % | N % | S % |
|---|---|---|---|---|
| calculated | 42.11 | 4.42 | 6.14 | 7.03 |
| found | 41.87 | 4.19 | 6.03 | 6.79 |

EXAMPLE 31

2-Oxo-6-(1-piperidylsulphonyl)-7-(trifluoromethyl)-1,2-dihydro-3-quinolylphosphonic Acid Diethyl Ester
The procedure is as for Example 29, replacing dipropylamine by piperidine in Step F.
Melting point 132–135° C.

EXAMPLE 32

2-Oxo-6-(1-piperidylsulphonyl)-7-(trifluoromethyl)-1,2-dihydro-3-quinolylphosphonic Acid
Melting point: >260° C.

Elemental microanalysis:

|  | C % | H % | N % | S % |
|---|---|---|---|---|
| calculated | 40.92 | 3.66 | 6.36 | 7.28 |
| found | 40.96 | 3.64 | 6.31 | 7.25 |

EXAMPLE 33

6-{[(Benzyloxy)amino]sulphonyl}-7-chloro-2-oxo-1,2-dihydro-3-quinolylphosphonic Acid Diethyl Ester
The procedure is as for Example 27, replacing methoxyamine hydrochloride by benzyloxyamine hydrochloride.
Melting point. 233–236° C.

Elemental microanalysis:

|  | C % | H % | N % | S % |
|---|---|---|---|---|
| calculated | 47.96 | 4.43 | 5.59 | 6.40 |
| found | 47.84 | 4.83 | 5.56 | 6.24 |

EXAMPLE 34

7-Chloro-6-[(hydroxyamino)sulphonyl]-2-oxo-1,2-dihydro-3-quinolylphosphonic Acid Diethyl Ester
1.35 ml (1.35 mmol) of a solution of 1M $BBr_3$ in $CH_2Cl_2$ are added dropwise to a suspension of 310 mg (0.655 mmol) of the product of the preceding Step in 30 ml of $CH_2Cl_2$ cooled to −60° C. The reaction mixture is allowed to return to −20° C. over a period of about 1 hour and is then poured into ice. The gelatinous white suspension is stirred and then filtered. The white solid is rinsed several times with water and then with ether. It is then suspended hot in acetonitrile and the resulting solid, corresponding to the title product, is filtered off.

Melting point: 285–290° C.

| Elemental microanalysis: | | | | |
|---|---|---|---|---|
| | C % | H % | N % | S % |
| calculated | 38.01 | 3.93 | 6.82 | 7.81 |
| found | 38.01 | 3.97 | 6.48 | 7.86 |

EXAMPLE 35
7-Chloro-6-[(hydroxyamino)sulphonyl]-2-oxo-1,2-dihydro-3-quinolylphosphonic Acid The procedure is as for Example 2 starting from the compound obtained in Example 34.

Melting point 285–290° C.

| Elemental microanalysis: | | | | | |
|---|---|---|---|---|---|
| | C % | H % | N % | S % | Cl % |
| calculated | 30.48 | 2.27 | 7.90 | 9.04 | 10.00 |
| found | 30.76 | 2.58 | 7.35 | 9.03 | 10.04 |

EXAMPLE 36
7-Chloro-6-[(cyclopropylamino)sulphonyl]-2-oxo-1,2-dihydro-3-quinolylphosphonic Acid Diethyl Ester The procedure is as for Example 1, replacing n-propylamine by cyclopropylamine in Step F.

Melting point: 261–263° C.

| Elemental microanalysis: | | | | | |
|---|---|---|---|---|---|
| | C % | H % | N % | S % | Cl % |
| calculated | 44.20 | 4.64 | 6.44 | 7.37 | 8.15 |
| found | 44.13 | 4.75 | 6.03 | 6.82 | 8.70 |

EXAMPLE 37
7-Chloro-6-[(cyclopropylamino)sulphonyl]-2-oxo-1,2-dihydro-3-quinolylphosphonic Acid The procedure is as for Example 2 starting from the compound obtained in Example 36.

Melting point: >300° C.

| Elemental microanalysis: | | | | | |
|---|---|---|---|---|---|
| | C % | H % | N % | S % | Cl % |
| calculated | 38.06 | 3.19 | 7.40 | 8.47 | 9.36 |
| found | 38.05 | 3.18 | 7.08 | 8.27 | 10.47 |

EXAMPLE 38
7-Chloro-6-[(isopropylamino)sulphonyl]-2-oxo-1,2-dihydro-3-quinolylphosphonic Acid Diethyl Ester The procedure is as for Example 1, replacing n-propylamine by isopropylamine in Step F.

Melting point: 239–240° C.

| Elemental microanalysis: | | | | | |
|---|---|---|---|---|---|
| | C % | H % | N % | S % | Cl % |
| calculated | 43.99 | 5.08 | 6.41 | 7.34 | 8.12 |
| found | 44.13 | 5.13 | 6.24 | 7.25 | 9.76 |

EXAMPLE 39
7-Chloro-6-[(isopropylamino)sulphonyl]-2-oxo-1,2-dihydro-3-quinolylphosphonic Acid The procedure is as for Example 2 starting from the compound obtained in Example 38.

Melting point: >300° C.

| Elemental microanalysis: | | | | | |
|---|---|---|---|---|---|
| | C % | H % | N % | S % | Cl % |
| calculated | 37.86 | 3.71 | 7.36 | 8.42 | 9.31 |
| found | 37.56 | 3.83 | 7.09 | 7.98 | 9.85 |

EXAMPLE 40
6-[(n-Butylamino)sulphonyl]-7-chloro-2-oxo-1,2-dihydro-3-quinolylphosphonic Acid Diethyl Ester The procedure is as for Example 1, replacing n-propylamine by n-butylamine in Step F.

Melting point: 229–230° C.

EXAMPLE 41
6-[(n-Butylamino)sulphonyl]-7-chloro-2-oxo-1,2-dihydro-3-quinolylphosphonic Acid The procedure is as for Example 2 starting from the compound obtained in Example 40.

Melting point: >300° C.

| Elemental microanalysis: | | | | | |
|---|---|---|---|---|---|
| | C % | H % | N % | S % | Cl % |
| calculated | 39.55 | 4.08 | 7.10 | 8.12 | 8.98 |
| found | 39.25 | 4.05 | 6.86 | 7.63 | 9.77 |

EXAMPLE 42
7-Chloro-6-[(ethylamino)sulphonyl]-2-oxo-1,2-dihydro-3-quinolylphosphonic Acid Diethyl Ester The procedure is as for Example 1, replacing n-propylamine by ethylamine in Step F.

Melting point: 225° C.

EXAMPLE 43
7-Chloro-6-[(ethylamino)sulphonyl]-2-oxo-1,2-dihydro-3-quinolylphosphonic Acid The procedure is as for Example 2 starting from the compound obtained in Example 42.

Melting point: >300° C.

| Elemental microanalysis: | | | | | |
|---|---|---|---|---|---|
| | C % | H % | N % | S % | Cl % |
| calculated | 36.03 | 3.30 | 7.64 | 8.74 | 9.67 |
| found | 35.95 | 3.44 | 7.31 | 8.16 | 10.51 |

EXAMPLE 44

7-Chloro-2-oxo-6-{[(2-phenylethyl)amino]sulphonyl}-1,2-dihydro-3-quinolylphosphonic Acid Diethyl Ester The procedure is as for Example 1, replacing n-propylamine by phenethylamine in Step F.

Melting point: 267–268° C.

Elemental microanalysis:

|  | C % | H % | N % | S % | Cl % |
|---|---|---|---|---|---|
| calculated | 50.56 | 4.85 | 5.61 | 6.43 | 7.11 |
| found | 50.71 | 4.94 | 5.68 | 6.22 | 7.92 |

EXAMPLE 45

7-Chloro-2-oxo-6-{[(2-phenylethyl)amino]sulphonyl}-1,2-dihydro-3-quinolylphosphonic Acid The procedure is as for Example 2 starting from the compound obtained in Example 44.

Melting point: >300° C.

Elemental microanalysis:

|  | C % | H % | N % | S % | Cl % |
|---|---|---|---|---|---|
| calculated | 46.11 | 3.64 | 6.33 | 7.24 | 8.01 |
| found | 45.60 | 3.65 | 6.18 | 7.06 | 8.53 |

EXAMPLE 46

2-Oxo-6-[(n-propylamino)sulphonyl]-7-(trifluoromethyl)-1,2-dihydro-3-quinolylphosphonic Acid Diethyl Ester The procedure is as for Step F of Example 29, replacing dipropylamine by n-propylamine.

Melting point: 218–220° C.

Elemental microanalysis:

|  | C % | H % | N % | S % |
|---|---|---|---|---|
| calculated | 43.41 | 4.71 | 5.96 | 6.82 |
| found | 43.39 | 4.65 | 5.82 | 6.80 |

EXAMPLE 47

2-Oxo-6-[(n-propylamino)sulphonyl]-7-(trifluoromethyl)-1,2-dihydro-3-quinolylphosphonic Acid The procedure is as for Example 2 starting from the compound obtained in Example 46.

Melting point: 277° C.

Elemental microanalysis:

|  | C % | H % | N % | S % |
|---|---|---|---|---|
| calculated | 37.69 | 3.41 | 6.76 | 7.74 |
| found | 37.74 | 3.57 | 6.74 | 8.10 |

EXAMPLE 48

6-[(Methylamino)sulphonyl]-2-oxo-7-(trifluoromethyl)-1,2-dihydro-3-quinolylphosphonic Acid Diethyl Ester The procedure is as for Step F of Example 29, replacing dipropylamine by methylamine.

Melting point: 142–145° C.

Elemental microanalysis:

|  | C % | H % | N % | S % |
|---|---|---|---|---|
| calculated | 40.73 | 4.10 | 6.33 | 7.25 |
| found | 40.64 | 4.01 | 6.18 | 7.11 |

EXAMPLE 49

6-[(Methylamino)sulphonyl]-2-oxo-7-(trifluoromethyl)-1,2-dihydro-3-quinolylphosphonic Acid The procedure is as for Example 2 starting from the compound obtained in Example 48.

Melting point: >300° C.

Elemental microanalysis:

|  | C % | H % | N % | S % |
|---|---|---|---|---|
| calculated | 34.21 | 2.61 | 7.25 | 8.30 |
| found | 34.56 | 2.66 | 7.34 | 8.59 |

Pharmacological Study

EXAMPLE A

Inhibition of the Current Induced by Administration of (R,S)-AMPA (10 $\mu$M) to *Xenopus oocytes* injected with mRNAs of Rat Cortex

*Xenopus oocytes* are injected with 50 ng of poly (A+) mRNAs isolated from the cerebral cortex of rat and incubated for 2 to 3 days at 18° C. to enable their protein expression. The influx currents induced by an administration of (R,S)-AMPA (10 $\mu$M) are measured in a medium having the composition: NaCl (82.5 mM), KCl (2.5 mM), CaCl$_2$ (1 mM), MgCl$_2$ (1 mM), NaH$_2$PO$_4$ (1 mM), HEPES (5 mM), pH 7.4, by the 2-electrode voltage clamp method (potential=−60 mV). The products of the present invention are administered in a concentration-dependent manner 30 seconds before and during administration of the agonist (R,S)-AMPA.

Their capacity to inhibit the current induced by (R,S)-AMPA is determined by the IC$_{50}$ values ($\mu$M), which represent the concentrations that inhibit by 50% the current induced by an administration of (R,S)-AMPA (10 $\mu$M).

The compounds of the invention demonstrate excellent inhibitory properties with IC$_{50}$ values ($\mu$M) of the order of 1.

EXAMPLE B

Audiogenic Convulsion Test in the DBA/2 Mouse

In the immature DBA/2 mouse, convulsive attacks can be triggered by subjecting the animal to stimulation with high-intensity high-frequency sound.

The AMPA-type glutamate receptor antagonists antagonise that type of convulsion in a dose-dependent manner (Chapman et al., Epilepsy Res., 1991, 9, 92–96). This test is used to study the anti-convulsive effects of the compounds of the present invention. In brief, immature DBA/2 mice (21–28 days) are exposed for 60 seconds to a noise of 105 dB and 18 kHz. This causes the appearance of clonic convulsions. The products being studied and the solvent are administered by the i.p. route 30 minutes before the start of the test in a volume of 0.1 ml/10 g. The $ED_{50}$ (dose that inhibits the occurrence of the convulsions by 50%) is determined for each compound using the method of Litchfield and Wicoxon (J. Pharmacol. Exp. Ther., 1949, 96, 99–113).

The compounds of the invention demonstrate an excellent capacity to inhibit the convulsions with $ED_{50}$ values of the order of 10 mg/kg ip.

EXAMPLE C
Nephrotoxicity Test in the Fischer Rat

Assessment of the renal impact of the compounds of the present invention is carried out in the adult male Fischer rat weighing 200–250 g. Fischer rats are anaesthetised using pentobarbital (Nembutal®, 60 mg/kg i.p.). 90 minutes after anaesthesia has been induced, the test compounds are administered by the intravenous route in doses of 3 and 10 mg/kg. 24 hours after administration, the animals are sacrificed, the plasma is removed and measurements of creatinaemia and uraemia are performed. Statistical analysis is carried out using single-factor variance analysis followed by a Newman-Keuls test, comparing the treated animals and animals having received only the carrier.

The compounds of the invention exhibit excellent renal tolerance, no toxic effect being obtained for doses less than or equal to 10 mg/kg i.v.

EXAMPLE D
Pharmaceutical composition

| | |
|---|---|
| 1000 tablets containing a dose of 5 mg of 7-chloro-2-oxo-6-[(n-propylamino)sulphonyl]-1,2-dihydro-3-quinolylphosphonic acid (Example 2) | 5 g |
| Wheat starch | 20 g |
| Maize starch | 20 g |
| Lactose | 30 g |
| Magnesium stearate | 2 g |
| Silica | 1 g |
| Hydroxypropylcellulose | 2 g |

We claim:
1. A compound selected from those of formula (I):

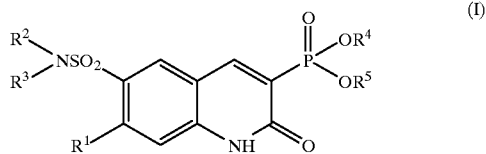

wherein:
$R^1$ represents halogen or trifluoromethyl,
$R^2$ represents hydrogen or alkyl or cycloalkyl,
$R^3$ represents alkyl, cycloalkyl, aryl, arylalkyl, alkoxy, aryloxy, arylalkoxy, hydroxy, aminoalkyl, alkylaminoalkyl, dialkylaminoalkyl, alkylcarbonyl, arylcarbonyl or arylalkylcarbonyl or $NHR^6$ (wherein $R^6$ represents hydrogen or alkyl, cycloalkyl, aryl, alkylcarbonyl, arylcarbonyl, arylalkyl or arylalkylcarbonyl),
or $R^2$ and $R^3$ together form with the nitrogen atom carrying them a ring having 5 to 6 carbon atoms, in which one of the carbon atoms can be replaced by oxygen, nitrogen or sulphur or by SO, $SO_2$ or $NR_a$ (wherein $R_a$ represents hydrogen or alkyl, cycloalkyl, aryl or arylalkyl),
$R^4$ and $R^5$, which may be identical or different, represent hydrogen or alkyl, cycloalkyl, aryl or arylalkyl or a group

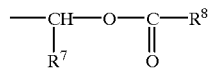

(wherein $R^7$ and $R^8$, which may be identical or different, represent hydrogen or alkyl, cycloalkyl or aryl),
it being understood that:
"alkyl" is understood to mean a linear or branched alkyl group containing from 1 to 6 carbon atoms,
"alkoxy" is understood to mean a linear or branched alkoxy group containing from 1 to 6 carbon atoms,
"cycloalkyl" is understood to mean a cyclic alkyl group containing from 3 to 8 carbon atoms,
"aryl" is understood to mean the groups phenyl or naphthyl, it being possible for those groups to be unsubstituted or substituted by from 1 to 3 groups selected from alkyl, cycloalkyl, hydroxy, alkoxy, amino, alkylamino, dialkylamino, cyano, nitro, polyhaloalkyl, $SO_2NR^9R^{10}$ (wherein $R^9$ and $R^{10}$, which may be identical or different, represent a hydrogen atom or an alkyl, cycloalkyl or aryl group) and halogen atoms,
its enantiomers and diastereoisomers and addition salts thereof with a pharmaceutically acceptable acid or base.

2. A compound of claim 1 wherein $R^1$ represents chlorine, their isomers and pharmaceutically acceptable addition salts thereof with an acid or a base.

3. A compound of claim 1 wherein $R^3$ represents alkyl, their isomers and addition salts thereof with a pharmaceutically acceptable acid or base.

4. A compound of claim 1 wherein $R^3$ represents aryl, their isomers and pharmaceutically acceptable addition salts thereof with an acid or a base.

5. A compound of claim 1 wherein $R^3$ represents a group NHCOR wherein R represents alkyl or aryl, their isomers and pharmaceutically acceptable addition salts thereof with an acid or a base.

6. A compound of claim 1 wherein $R^2$ represents hydrogen, their isomers and pharmaceutically acceptable addition salts thereof with an acid or a base.

7. A compound of claim 1 wherein $R^4$ and $R^5$ simultaneously represent hydrogen, their isomers and pharmaceutically acceptable addition salts thereof with an acid or a base.

8. A compound of claim 1 selected from 7-chloro-2-oxo-6-[(propylamino)sulphonyl]-1,2-dihydro-3-quinolylphosphonic acid, and 7-chloro-6-[(methylamino)sulphonyl]-2-oxo-1,2-dihydro-3-quinolylphosphonic acid, their isomers and pharmaceutically acceptable addition salts thereof with an acid or a base.

9. A compound of claim 1 selected from 7-chloro-6-[(2-{4-[(dipropylamino)sulphonyl]benzoyl}hydrazino)sulphonyl]-2-oxo-1,2-dihydro-3-quinolylphosphonic acid, its isomers and pharmaceutically acceptable addition salts thereof with an acid or a base.

10. A compound of claim 1 selected from 7-chloro-6-({[2-(dimethylamino)ethyl]amino}sulphonyl)-2-oxo-1,2- dihydro-3-quinolylphosphonic acid hydrobromide, its isomers and pharmaceutically acceptable addition salts thereof with an acid or a base.

11. A compound of claim 1 selected from 6-(anilinosulphonyl)-7-chloro-2-oxo-1,2-dihydro-3-quinolylphosphonic acid, its isomers and pharmaceutically acceptable addition salts thereof with an acid or a base.

12. A compound of claim 1 selected from 6-[(2-benzoylhydrazino)sulphonyl]-7-chloro-2-oxo-1,2-dihydro-3-quinolylphosphonic acid, its isomers and pharmaceutically acceptable addition salts thereof with an acid or a base.

13. A method for treating an animal or human living body afflicted with acute or chronic pathological condition associated with hyperactivation of the neurotransmission paths to the excitatory amino acids comprising the step of administering to the living body an AMPA receptor inhibiting amount of a compound of claim 1 which is effective for alleviation of said conditions.

14. A method of claim 13 wherein the pathological condition is with cerebrovascular accident, cerebral or spinal traumatism, epilepsy, or chronic neurodegenerative disease.

15. A pharmaceutical composition useful in the method for treating an animal or human living body afflicted with acute or chronic pathological condition associated with hyperactivation of the excitatory amino acid AMPA receptor inhibiting amount of a compound as claimed in claim 1, together with one or more pharmaceutically acceptable excipients or vehicles.

16. A pharmaceutical composition comprising a compound as claimed in claim 1, together with one or more pharmaceutically acceptable excipients or vehicles.

* * * * *

UNITED STATES PATENT AND TRADEMARK OFFICE
CERTIFICATE OF CORRECTION

PATENT NO. : 6,486,143 B2
DATED : November 26, 2002
INVENTOR(S) : Alex Cordi et al.

It is certified that error appears in the above-identified patent and that said Letters Patent is hereby corrected as shown below:

<u>Title page,</u>
Item [57], ABSTRACT,
Last line, "Medicaments" should be -- and methods for using the same --

<u>Column 22,</u>
Claims 2,3,4,5,6 and 7, remove ", their isomers and pharmaceutically acceptable addition salts thereof with and acid or base"

<u>Column 23, lines 12-16 and Column 24, lines 1 and 2,</u>
Claim 13 should read as follows;
-- A method for treating an animal or human living body afflicted with
   acute or chronic pathological condition associated with
   hyperactivation of the excitatory amino acid neurotransmission
   pathways comprising the step of administering to the living body an
   AMPA receptor inhibiting amount of a compound of claim 1 which is
   effective for alleviation of said condition. --

<u>Column 24,</u>
Line 9, insert -- neurotransmission pathways comprising as active principle an -- before "AMPA receptor".

Signed and Sealed this

Twenty-fourth Day of June, 2003

JAMES E. ROGAN
*Director of the United States Patent and Trademark Office*